(12) United States Patent
Agassi et al.

(10) Patent No.: US 11,398,232 B1
(45) Date of Patent: Jul. 26, 2022

(54) NATURAL LANGUAGE UNDERSTANDING OF CONVERSATIONAL SOURCES

(71) Applicant: CERNER INNOVATION, INC., Kansas City, KS (US)

(72) Inventors: Emin Agassi, Blue Bell, PA (US); Tanuj Gupta, Leawood, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 116 days.

(21) Appl. No.: 16/720,641

(22) Filed: Dec. 19, 2019

Related U.S. Application Data

(60) Provisional application No. 62/783,695, filed on Dec. 21, 2018, provisional application No. 62/783,688, filed on Dec. 21, 2018.

(51) Int. Cl.
| | | |
|---|---|---|
| *G10L 15/22* | (2006.01) | |
| *G16H 10/60* | (2018.01) | |
| *G06F 3/16* | (2006.01) | |
| *G10L 15/18* | (2013.01) | |
| *G10L 15/30* | (2013.01) | |

(52) U.S. Cl.
CPC .............. *G10L 15/22* (2013.01); *G06F 3/167* (2013.01); *G10L 15/1815* (2013.01); *G10L 15/1822* (2013.01); *G16H 10/60* (2018.01); *G10L 15/30* (2013.01); *G10L 2015/223* (2013.01)

(58) Field of Classification Search
CPC . G10L 15/22; G10L 15/1815; G10L 15/1822; G10L 15/30; G10L 2015/223; G16H 10/60; G06F 3/167
See application file for complete search history.

(56) References Cited

U.S. PATENT DOCUMENTS

| | | |
|---|---|---|
| 7,379,946 B2 | 5/2008 | Carus et al. |
| 7,881,957 B1 | 2/2011 | Cohen et al. |
| 7,885,811 B2 | 2/2011 | Zimmerman et al. |
| 8,170,897 B1 | 5/2012 | Cohen et al. |
| 8,185,553 B2 | 5/2012 | Carus et al. |
| 8,209,183 B1 | 6/2012 | Patel et al. |
| 8,255,258 B1 | 8/2012 | Cohen et al. |
| 8,374,865 B1 | 2/2013 | Biadsy et al. |
| 8,428,940 B2 | 4/2013 | Kristjansson et al. |
| 8,498,892 B1 | 7/2013 | Cohen et al. |
| 8,510,340 B2 | 8/2013 | Carus et al. |
| 8,612,211 B1 | 12/2013 | Shires et al. |

(Continued)

OTHER PUBLICATIONS

Chiu, C. C., Tripathi, A., Chou, K., Co, C., Jaitly, N., Jaunzeikare, D., . . . & Tansuwan, J. (2017). Speech recognition for medical conversations. arXiv preprint arXiv:1711.07274.

(Continued)

*Primary Examiner* — Huyen X Vo
*Assistant Examiner* — Athar N Pasha
(74) *Attorney, Agent, or Firm* — Shook, Hardy & Bacon L.L.P.

(57) ABSTRACT

Methods and systems for natural language processing/understanding of voice conversations are provided. Using natural language processing, a clinical condition is extracted from a voice conversation. A clinical ontology identifies clinical concepts associated with the clinical conditions. The clinical concepts are classified for documentation. The clinical concepts are searched and validated from within an individual's longitudinal record.

14 Claims, 11 Drawing Sheets

(56) References Cited

U.S. PATENT DOCUMENTS

| | | |
|---|---|---|
| 8,694,335 B2 | 4/2014 | Yegnanarayanan |
| 8,700,395 B2 | 4/2014 | Zimmerman et al. |
| 8,738,403 B2 | 5/2014 | Flanagan et al. |
| 8,756,079 B2 | 6/2014 | Yegnanarayanan |
| 8,768,723 B2 | 7/2014 | Montyne et al. |
| 8,782,088 B2 | 7/2014 | Carus et al. |
| 8,788,289 B2 | 7/2014 | Flanagan et al. |
| 8,799,021 B2 | 8/2014 | Flanagan et al. |
| 8,831,957 B2 | 9/2014 | Taubman et al. |
| 8,878,773 B1 | 11/2014 | Bozarth |
| 8,880,406 B2 | 11/2014 | Santos-Lang et al. |
| 8,924,211 B2 | 12/2014 | Ganong, III et al. |
| 8,953,886 B2 | 2/2015 | King et al. |
| 8,972,243 B1 | 3/2015 | Strom et al. |
| 8,977,555 B2 | 3/2015 | Torok et al. |
| 9,058,805 B2 | 6/2015 | Aleksic et al. |
| 9,117,451 B2 | 8/2015 | Fructuoso et al. |
| 9,129,013 B2 | 9/2015 | Delaney et al. |
| 9,135,571 B2 | 9/2015 | Delaney et al. |
| 9,147,054 B1 | 9/2015 | Beal et al. |
| 9,152,763 B2 | 10/2015 | Darus et al. |
| 9,240,187 B2 | 1/2016 | Torok et al. |
| 9,257,120 B1 | 2/2016 | Alvarez Guevara et al. |
| 9,269,012 B2 | 2/2016 | Fotland |
| 9,292,089 B1 | 3/2016 | Sadek |
| 9,304,736 B1 | 4/2016 | Whiteley et al. |
| 9,318,104 B1 | 4/2016 | Fructuoso et al. |
| 9,324,323 B1 | 4/2016 | Bikel et al. |
| 9,343,062 B2 | 5/2016 | Ganong, III et al. |
| 9,378,734 B2 | 6/2016 | Ganong, III et al. |
| 9,384,735 B2 | 7/2016 | White et al. |
| 9,420,227 B1 | 8/2016 | Shires et al. |
| 9,424,840 B1 | 8/2016 | Hart et al. |
| 9,443,509 B2 | 9/2016 | Ganong, III et al. |
| 9,466,294 B1 | 10/2016 | Tunstall-Pedoe et al. |
| 9,538,005 B1 | 1/2017 | Nguyen et al. |
| 9,542,944 B2 | 1/2017 | Jablokov et al. |
| 9,542,947 B2 | 1/2017 | Schuster et al. |
| 9,552,816 B2 | 1/2017 | VanLund et al. |
| 9,563,955 B1 | 2/2017 | Kamarshi et al. |
| 9,569,594 B2 | 2/2017 | Casella dos Santos |
| 9,570,076 B2 | 2/2017 | Sierawski et al. |
| 9,601,115 B2 | 3/2017 | Chen et al. |
| 9,678,954 B1 | 6/2017 | Cuthbert et al. |
| 9,679,107 B2 | 6/2017 | Cardoza et al. |
| 9,721,570 B1 | 8/2017 | Beal et al. |
| 9,786,281 B1 | 10/2017 | Adams et al. |
| 9,792,914 B2 | 10/2017 | Alvarez Guevara et al. |
| 9,805,315 B1 | 10/2017 | Cohen et al. |
| 9,898,580 B2 | 2/2018 | Flanagan et al. |
| 9,904,768 B2 | 2/2018 | Yegnanarayanan |
| 9,911,418 B2 | 3/2018 | Chi |
| 9,916,420 B2 | 3/2018 | Cardoza et al. |
| 9,922,385 B2 | 3/2018 | Yegnanarayanan |
| 9,971,848 B2 | 5/2018 | D'Souza et al. |
| 10,032,127 B2 | 7/2018 | Habboush et al. |
| 10,347,117 B1* | 7/2019 | Capurro .................. A61G 12/00 |
| 10,602,974 B1 | 3/2020 | Govindjee et al. |
| 2011/0178931 A1* | 7/2011 | Kia .......................... G16H 10/60 705/50 |
| 2015/0142418 A1* | 5/2015 | Byron .................... G06F 40/232 704/9 |
| 2015/0340033 A1 | 11/2015 | Di Fabbrizio et al. |
| 2018/0012604 A1 | 1/2018 | Guevara et al. |
| 2018/0308490 A1* | 10/2018 | Lim ........................ G10L 15/26 |
| 2019/0121532 A1* | 4/2019 | Strader .................... G10L 15/26 |
| 2019/0130073 A1* | 5/2019 | Sun ..................... G06K 9/00442 |
| 2019/0206524 A1* | 7/2019 | Baldwin ................ G06F 40/30 |
| 2019/0272919 A1* | 9/2019 | Frandsen ................ H04W 4/12 |
| 2019/0287665 A1 | 9/2019 | Forsberg et al. |

OTHER PUBLICATIONS

Pre-Interview First Office action received for U.S. Appl. No. 16/720,632, dated Feb. 17, 2022, 4 pages.

* cited by examiner

NATURAL LANGUAGE UNDERSTANDING OF CONVERSATIONAL SOURCES

CROSS REFERENCE TO RELATED APPLICATIONS

This application claims the benefit of priority to U.S. Provisional Application No. 62/783,688, filed on Dec. 21, 2018, entitled "Natural Language Understanding of Conversational Sources," and U.S. Provisional Application No. 62/783,695, filed on Dec. 21, 2018, entitled "Document Generation from Conversational Sources," the entirety of each of which is incorporated herein by reference.

BACKGROUND

Clinicians are spending an increasing amount of time within clinical documentation systems documenting their findings rather than being able to focus time spent with a patient. Many techniques have been utilized to try and reduce the amount of time spent on documentation or other documentation-type tasks (e.g., order entry). Such techniques include natural language processing to extract and understand content from documents. However, there is no current solution to identify context from spoken conversations and, in turn, organize the extracted data (from the spoken conversation) into organized, intelligent groupings that may be utilized for documentation or even document generation. Natural language processing/understanding techniques have not yet been utilized for extraction of content from clinical-based voice conversations.

SUMMARY

Systems, methods and computer-readable media are provided for performing natural language understanding on voice conversations. Interactions between a clinician (or any healthcare provider) and a patient (or individual) are, in large part, spoken interactions. Clinicians collect a history of a patient by asking a series of questions and receiving a response. Clinicians gain insight into a reason for a visit or any issues a patient is having by, again, asking questions of the patient and obtaining responses. Many other variables are also collected orally from a patient during a voice conversation.

In an embodiment, during a voice conversation, the voice conversation is evaluated using natural language processing/understanding ("NLP/NLU") to identify and extract one or more clinical concepts, such as a clinical condition. Once the clinical concepts are identified and extracted, one or more clinical ontologies is determined. These ontologies may be used to intelligently classify the clinical concepts from the voice conversation into one or more classification groups. The system may be able to use the classification groups to generate documents from the encounter, to generate documentation items/action items, validate scribe output with information within the EHR, and the like. In this way, the voice conversation and the patient's EHR are utilized to identify and incorporate information about the clinical concepts into the patient's EHR, identify potential errors during the encounter (either collected from the voice conversation or generated from the scribe), generate documents and/or documentation from the voice conversation, and the like. A scribe, as used herein, refers to a virtual scribe.

In some embodiments, a validation may be performed for the extracted clinical condition from the voice conversation based on whether the clinical condition could be correlated with structured data in the patient's longitudinal record (EHR). The validation may also be performed with respect to any output from the system using the voice conversation such as, for instance, orders, documentation, etc. The validation includes corroborating the voice conversation outputs with the patient's longitudinal record. Based on the validation, the output may be "flagged" as an error or unvalidated output. The "flag" may be in the form of an alert that is generated or a visual indicator associated with the unvalidated output to indicate that the output is not validated. A goal of the present disclosure is to provide natural language understanding of voice conversations in order to generate structured, usable documents and documentation-type action items (e.g., orders, assessments, clinician notes, etc.) and to provide safeguards for identifying potential problems with a voice conversation output when there is a lack of corroborating evidence.

BRIEF DESCRIPTION OF THE DRAWINGS

The present invention is described in detail below with reference to the attached drawing figures, wherein:

FIGS. 2-8 depict exemplary scribe user interfaces in accordance with embodiments herein.

DETAILED DESCRIPTION

Figure 1A:
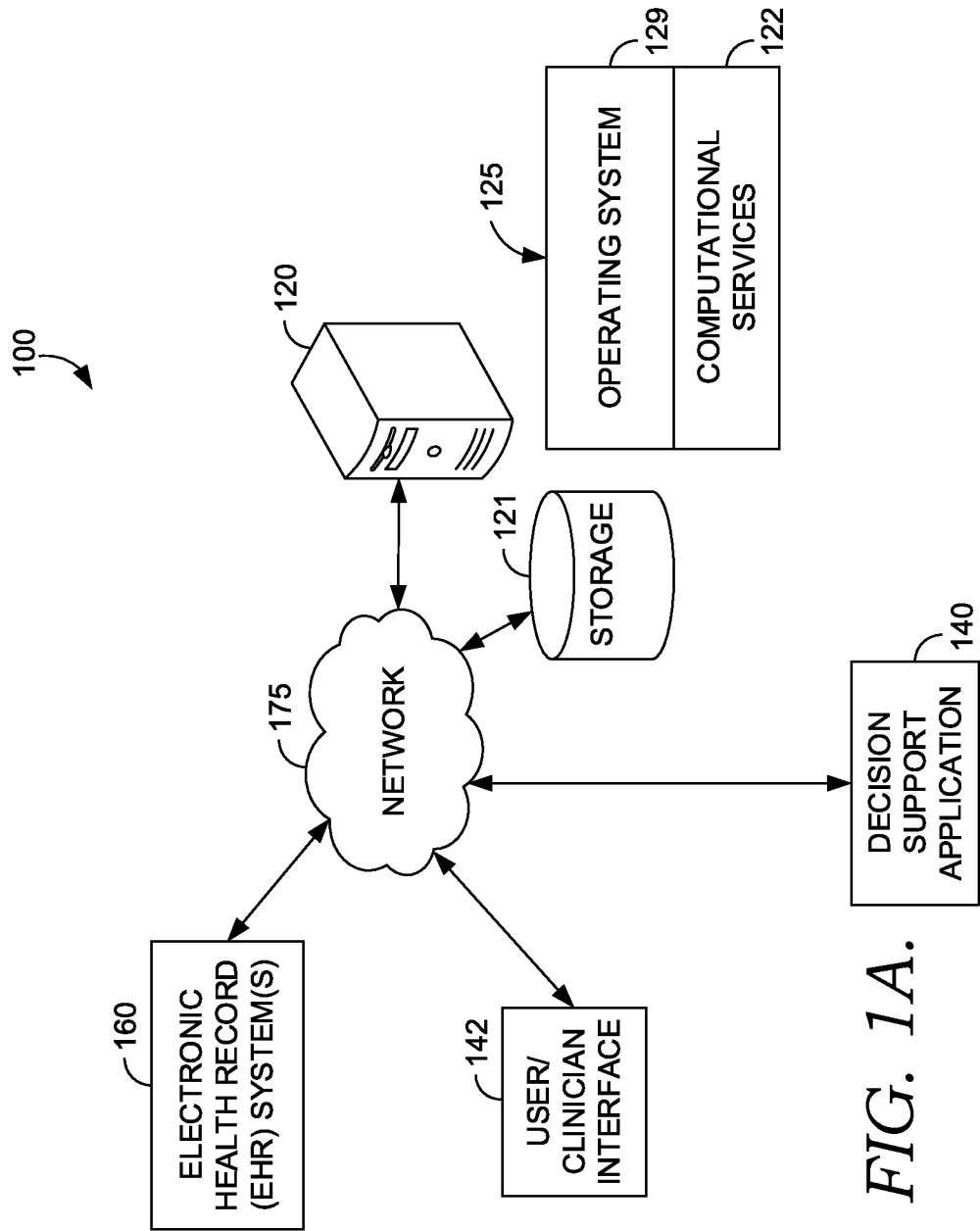
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, natural language processing/understanding (NLP/NLU) may be used to identify and extract, from a voice conversation, one or more clinical concepts. Once the clinical concepts are identified and extracted, one or more clinical ontologies may be used to identify one or more clinical concepts related to the clinical conditions identified from the voice conversation.

The ontologies may be used to intelligently classify the one or more clinical conditions/concepts from the voice conversation into one or more classification groups. A scribe output may also be generated by the system/scribe. The scribe output may include, but is not limited to, a transcription of the voice conversation, documents, documentation items (to be documented into a patient's record), orders/action items, and the like.

In embodiments, the scribe output is validated with corroborating evidence from the patient's EHR, for example. For instance, a patient may say they are currently on no medications. The clinical concept "medications" is identified and the negative response is noted by the computerized scribe. Upon validation, however, the scribe notes that there are medications listed in the patient's EHR (or any other validating source). The system would identify the error and notify the user. The notification can be a real-time notification/alert (e.g., a pop-up alert) including a visual indicator that would indicate an error (e.g., an exclamation mark, changing the font color or type, highlighting, etc.), an audio notification, and the like. Further, in addition to the notification, the contradicting information (e.g., the output of the scribe and the non-corroborating information from the validation source) may be provided in association with the notification.

In this way, the voice conversation and the patient's EHR are utilized to identify and incorporate information about the clinical conditions or concepts into the patient's EHR, identify potential errors generated by the scribe during the encounter, identify potential errors collected from the voice conversation, generate documents and/or documentation items from the voice conversation, and the like.

As used herein, the term "EHR" or "longitudinal EHR" refers to an electronic health record for an individual with documentation spanning across multiple encounters for the individual or at least one encounter prior to the current one for which the current electronic document is created. Accordingly, the documentation within the longitudinal EHR may be recorded at different times. The longitudinal EHR may also comprise at least some structured data. The data therein may be time and date stamped such that, in addition to providing the substance of those previous encounters, the longitudinal EHR provides a time line of the patient's care and, in some instances, one or more time series of physiological variables and clinical concepts related to the patient.

Accordingly, one aim of embodiments of this disclosure relates to applying NLP/NLU systems and clinical ontologies to voice conversations to provide validated clinical outputs. Current technologies fail to capture, recognize, or incorporate into structured, usable data, valuable longitudinal patient information from a voice conversation. The present disclosure seeks to extract information from a voice conversation, using NLP/NLU and a clinical ontology, and utilize information from the patient's electronic health record to validate the output. Embodiments perform NLP/NLU on unstructured voice data to parse and extract discrete clinical elements, including a clinical condition associated with the patient. Additional information may be parsed from the voice conversation such as the number of speakers, the role of the speakers, who is speaking at what time, a specialty of the speaker, and the like. Additionally, the system can apply a time function such that concepts identified are classified as a past issue or a present issue (e.g., "I had some stomach pain but it seems better now. Headaches are still a concern" would result in a past stomach pain problem and a present headache problem).

A clinical ontology associated with the clinical condition that is extracted from the voice conversation is retrieved, and one or more related clinical concepts (i.e., related to the clinical conditions), such as clinical findings, symptoms, problems, observations, medications, and procedures, are identified using the clinical ontology. The information extracted from the voice conversation is then classified into one or more classification groups.

Today, well-formatted documents are the sources from which clinical concepts are extracted. This makes it very easy to identify a problem, a reason for a visit, etc., because they are organized in a document based on those classifications. This cannot be said for voice conversations. The voice data is unstructured and subject to additional difficulties associated with conversations that does not apply to documents such as, slang terminology, interruptions, unfinished sentences, dialects, speaking preferences or differences, etc.

Existing technology is unable to capture context from clinical voice conversations for at least these reasons. Furthermore, clinical context is vastly different from typical "utterances" that are captured by today's voice assistants. For instance, there are only a few ways to ask "what is the weather for today" and the response is predetermined but there are numerous ways to ask "how are you feeling today" and even more ways to respond to that question. Furthermore, many terms used in clinical conversations may be referred to as many different things. For instance, "cold" may refer to a chill (i.e., temperature) or an upper respiratory infection, which also goes by many different names. Even once a correct term is identified in a clinical conversation, it can then be associated with many different options. For example, "pneumonia" may trigger numerous coding options in ICD-10, as shown in the below table.

| | | |
|---|---|---|
| J18, Pneumonia, Unspecified Organism | | Non-Billable |
| J18.0 | Bronchopneumonia, unspecified organism | Billable |
| J18.1 | Lobar pneumonia, unspecified organism | Billable |
| J18.2 | Hypostatic pneumonia, unspecified organism | Billable |
| J18.8 | Other pneumonia, unspecified organism | Billable |
| J18.9 | Pneumonia, unspecified organism | Billable |

In addition to many different types of pneumonia triggered by the use of the word "pneumonia" there are several exceptions as well. For instance, there are special codes for aspiration pneumonia due to anesthesia during pregnancy (use Code 029), aspiration pneumonia due to solids and liquids (use Code J69), congenital pneumonia (use Code P23.0), and the like. The list goes on with various coding options for pneumonia. While coding is not the only application for the present invention—far from it—it is indicative of the vast vocabulary associated with clinical settings and clinical concepts.

Besides the expansive clinical vocabulary generally, many situations call for specific terms and will result in different concepts. For instance, a conversation in an oncology setting is going to be different than a conversation in a pathology setting. This is yet another example of the expansive clinical vocabulary that must be processed correctly to obtain accurate outputs.

Thus, conventional speech-to-text technologies are not capable of extracting context from clinical voice conversations, at least, because they fail to integrate voice conversations or commands with a patient's electronic health record (EHR). Additionally, current speech-to-text technologies fail to capture, recognize, and transcribe voice conversations into structured, usable data that may be incorporated into the patient's EHR.

Referring now to the drawings in general and, more specifically, referring to FIG. 1A, an aspect of an operating environment 100 is provided suitable for practicing an embodiment of this disclosure. Certain items in block-diagram form are shown more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure aspects of the invention. Thus, for readability, items are shown and referenced in the singular (while fully contemplating, where applicable, the plural). Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

As shown in FIG. 1A, example operating environment 100 provides an aspect of a computerized system for compiling and/or running an embodiment for providing natural language processing or understanding of voice conversations. Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages, such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, the functions performed by these components, or the services carried out by these components may be implemented at appropriate abstraction layer(s), such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that, in some embodiments, functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems, and may be implemented in computer system 120. Similarly, EHR system 160 may perform functions for two or more of the EHR systems (not shown).

Continuing with FIG. 1A, network 175 may comprise the Internet, and/or one or more public networks, private networks, other communications networks, such as a cellular network or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health-related records, which may be stored on storage 121, and may further include one or more computers or servers that facilitate the storing and retrieval of the health records. In some embodiments, EHR system 160 and/or other records systems may be implemented as a cloud-based platform or may be distributed across multiple physical locations. EHR system 160 may further include record systems that store real-time or near real-time patient (or user) information, such as wearable sensor or monitor, bedside, or in-home patient monitors or sensors, for example. Although FIG. 1A depicts an example EHR system 160, it is contemplated that an embodiment relies on natural language process (NLP) application 140 for storing and retrieving patient record information.

Example operating environment 100 further includes a user/clinician interface 142 and NLP application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 may be communicatively coupled to EHR system 160 directly. An embodiment of NLP application 140 comprises a software application or set of applications (which may include programs, routines, functions, or computer-performed services) residing on a client computing device, such as a personal computer, laptop, smartphone, tablet, or mobile computing device or application 140 may reside on a remote server communicate coupled to a client computing device. In an embodiment, application 140 is a Web-based application or applet and may be used to provide or manage user services provided by an embodiment of the technologies described herein, which may be used to provide, for example, semantic analysis on voice conversations. In some embodiments, application 140 includes or is incorporated into a computerized decision support tool. Further, some embodiments of application 140 utilize user/clinician interface 142.

In some embodiments, application 140 and/or interface 142 facilitate accessing and receiving information from a user or healthcare provider about a specific patient or set of patients, according to the embodiments presented herein. Embodiments of application 140 also may facilitate accessing and receiving information from a user or healthcare provider about a specific patient, caregiver, or population including historical data; healthcare resource data; variables measurements; time series information; reference information, including clinical ontologies; and relational databases, as described herein; or other health-related information, and facilitates the display of results of the enhanced language process as described herein.

In some embodiments, user/clinician interface 142 may be used with application 140, such as described above. One embodiment of user/clinician interface 142 comprises a user interface that may be used to facilitate access by a user (including a healthcare provider or patient) to an assigned clinician, patient, or patient population. One embodiment of interface 142 takes the form of a graphical user interface and application, which may be embodied as a software application (e.g., NLP application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application, which may take the form of an applet or app, or a set of applications usable to manage user services provided by an embodiment of the technologies described herein.

In some embodiments, interface 142 may facilitate providing output of the scribe; providing instructions or outputs of other actions described herein; providing notifications; and logging and/or receiving other feedback from the user/caregiver, in some embodiments.

Example operating environment 100 further includes computer system 120, which may take the form of one or more servers and which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers, and may be distributed across the other components of example operating environment 100. For example, aspects of NLP application 140 or user/clinician interface 142 may operate on or utilize computer system 120. Similarly, a portion of computing system 120 may be embodied on user/clinician interface 142, application 140, and/or EHR system 160. In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud and is capable of hosting a number of services such as 122. Some embodiments of operating system 129 comprise a distributed adaptive agent operating system. Embodiments of services may run as local services or may be distributed across one or more components of operating environment 100, in the cloud, on one or more personal computers or servers such as computer system 120, and/or a computing device running interface 142 or application 140. In some embodiments, interface 142 and/or application 140 operate in conjunction with software stack 125.

Computational services 122 may perform statistical or computing operations such as computing functions or routines for processing of extracted information, as further described herein. Computational services 122 also may include natural language processing services (not shown) such as Discern nCode™ developed by Cerner Corporation, or similar services. In an embodiment, computational services 122 include the services or routines that may be embodied as one or more software agents or computer software routines. Computational services 122 also may include services or routines for utilizing one or more models, including logistic models. Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a patient (or information for multiple patients), including raw and processed patient data; variables associated with patient diagnoses; and information pertaining to clinicians and staff, include user preferences. It is contemplated that the term "data" includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
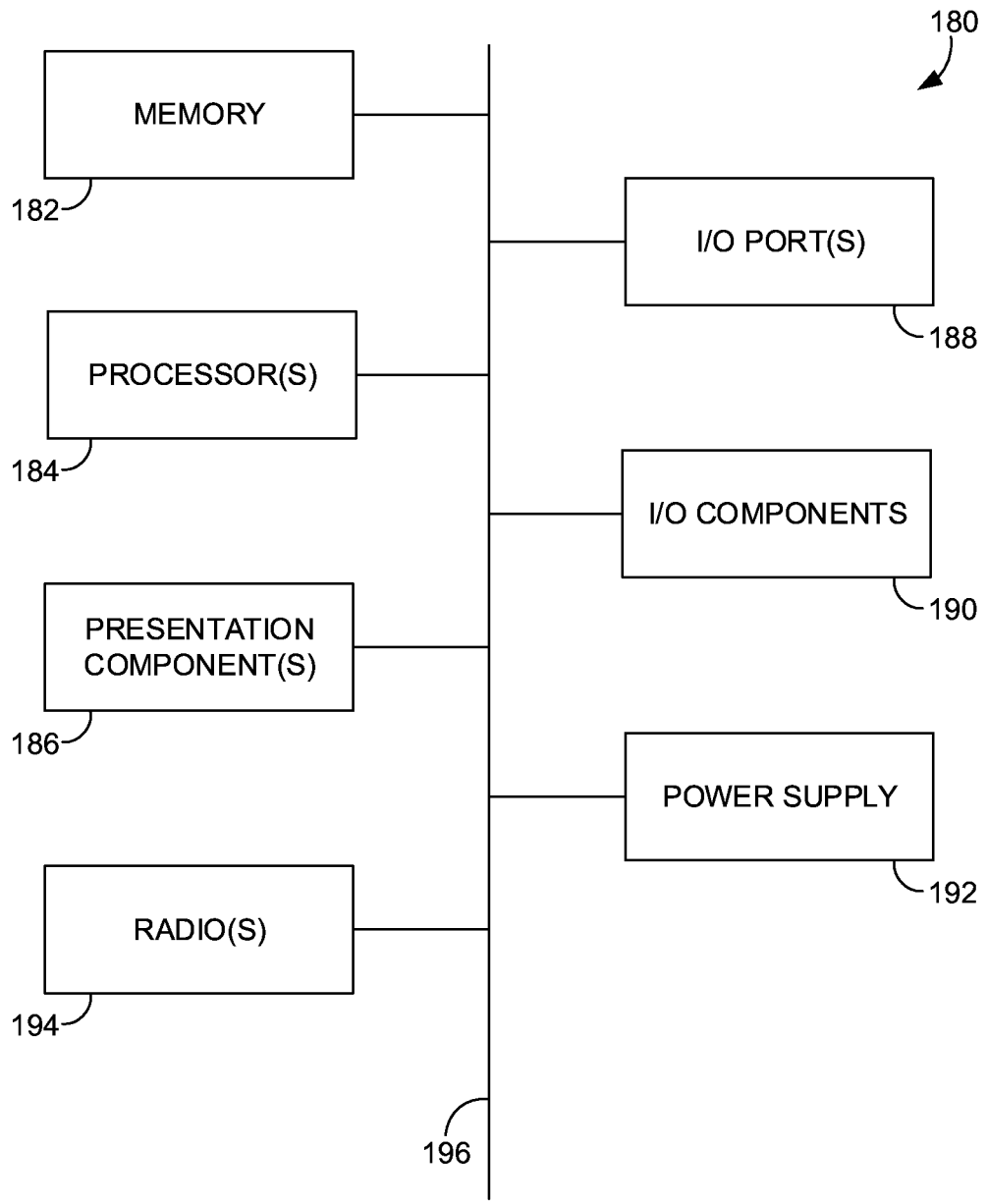

Turning briefly to FIG. 1B, there is shown one example embodiment of computing system 180 representative of a system architecture that is suitable for computer systems such as computer system 120. Computing device 180 includes a bus 196 that directly or indirectly couples the following devices: memory 182, one or more processors 184, one or more presentation components 186, input/output (I/O) ports 188, input/output components 190, radio 194, and an illustrative power supply 192. Bus 196 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1B and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 182 includes computer-storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 190. Presentation component(s) 186 present data indications to a user or other device. Exemplary presentation components include a display device, speaker, printing component, vibrating component, etc.

In some embodiments, computing system 194 comprises radio(s) 194 that facilitates communication with a wireless-telecommunications network. Illustrative wireless telecommunications technologies include CDMA, GPRS, TDMA, GSM, and the like. Radio 194 may additionally or alternatively facilitate other types of wireless communications including Wi-Fi, WiMAX, LTE, or other VoIP communications. As can be appreciated, in various embodiments, radio 194 can be configured to support multiple technologies and/or multiple radios can be utilized to support multiple technologies.

I/O ports 188 allow computing system 180 to be logically coupled to other devices, including I/O components 190, some of which may be built in. Illustrative components include a microphone, joystick, game pad, satellite dish, scanner, printer, wireless device, etc. The I/O components 190 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In application, the systems described herein apply NLP and clinical ontologies to voice conversational sources to provide structured, usable output. Initially, a voice conversation is captured. A voice conversation can include one or more voice inputs. The voice inputs can be separated based on, for example, speaker, role of speaker, location of speaker, specialty of speaker, and the like. The voice input(s) can be captured automatically by a system that is, for instance, continuously listening. The voice input(s) can also be captured upon receiving an initiation cue to begin listening to the environment.

The voice conversation (and inputs therein) may be transformed to text (e.g., transcript) using speech recognition software currently available. The transcript may be searchable. The transcript may be dynamically generated in real-time or near real-time. The conversation is collected and stitched together. Memory for speech-to-text technology is only capable of holding a predetermined amount of data so the recordings are typically smaller chunks. There is a technological cap on the memory space, resulting in the conversation being chopped at predetermined intervals (e.g., segment thresholds). The present technology, however, segments the conversation into much smaller intervals than the predetermined segment threshold. For instance, if the memory threshold is 1 minute, the present technology segments the conversation into smaller pieces, such as 15-20 second intervals. This is a configurable period of time. By segmenting the conversation to be transcribed into much smaller parts, the output is provided much quicker. It is not ideal to wait an entire minute for output.

The present technology also accounts for potential loss of conversation at segment thresholds. For example, if a recording stops at 1 min and then restarts, there is inevitably data lost in the time it takes to start and restart. The present invention stitches together various segments to avoid data loss. A period of time prior to the segment ending may be identified and added to a next segment (e.g., one second prior to the segment end time may be added to the segment). Alternatively, the last audio spoken may be identified and the segment remaining after the last audio spoken may be added to the next segment. This information is identified to stitch to the next segment to avoid loss of audio. In other words, if a segments ends at 17 seconds, the last piece of audio where a word ended is stitched onto or added to the next segment and then transcribed. Alternatively, if a segment ends at 17 seconds, the audio after 16 seconds may be stitched onto the next segment.

Once transcribed, the unstructured transcript of the voice conversation is then processed by NLP/NLU to identify/extract one or more clinical concepts from the voice conversation. Clinical concepts, as used herein, generally refers to any clinical issue associated with a clinical encounter including, but not limited to, a diagnosis, a problem, a symptom, etc. For instance, a patient stating that they have Alzheimer's disease would trigger identification of Alzheimer's as a problem or diagnosis. The one or more clinical concepts is parsed and extracted from the transcript of the voice conversation including unstructured clinical data in conversational format. Put simply, the transcript is a transcription of the spoken words of the voice conversation. There are no headings, no mention of appropriate clinical concepts or classifications to use for documentation, etc. It is a transcript of a conversation that is occurring during a patient encounter between, for instance, a patient and a provider. The transcript is not a structured document and is not provided in a structured, useable format for, for instance, documentation.

In addition to extraction of clinical conditions/concepts, NLP/NLU may also be utilized to identify context within the voice conversation. Context may be identified using a role of a speaker, a number of speakers, the specialty of the speaker, etc. For example, if a speaker is identified as an oncology clinician, a different context would apply than if the speaker were identified as, for example, a dermatologist. Additionally, voice inputs made by a surgeon would apply a different context than if identified from, for instance, a primary care provider.

The extracted concepts can be positive or negative. For instance, a conversation including the phrase "I was recently diagnosed with Alzheimer's and require a lot of assistance at home" would trigger identification of the concept "Alzheimer's" with a POSITIVE note as the patient has identified being identified with Alzheimer's. Conversely, a conversation regarding a wound, for example, where a clinician notes that "it doesn't look infected" may trigger identification of an "infectious disease" concept and a NEGATIVE note as the clinician verbally stated it did not look like an infection.

Additionally, as previously mentioned, NLP/NLU can apply a time function to the concepts to identify if the concept is a present issue or a past issue. For instance, a statement that "my other doctor sent me for a chest X-ray" may be identified as a past test. This temporal analysis can be performed on the extracted concepts of the voice inputs.

Figure 2:
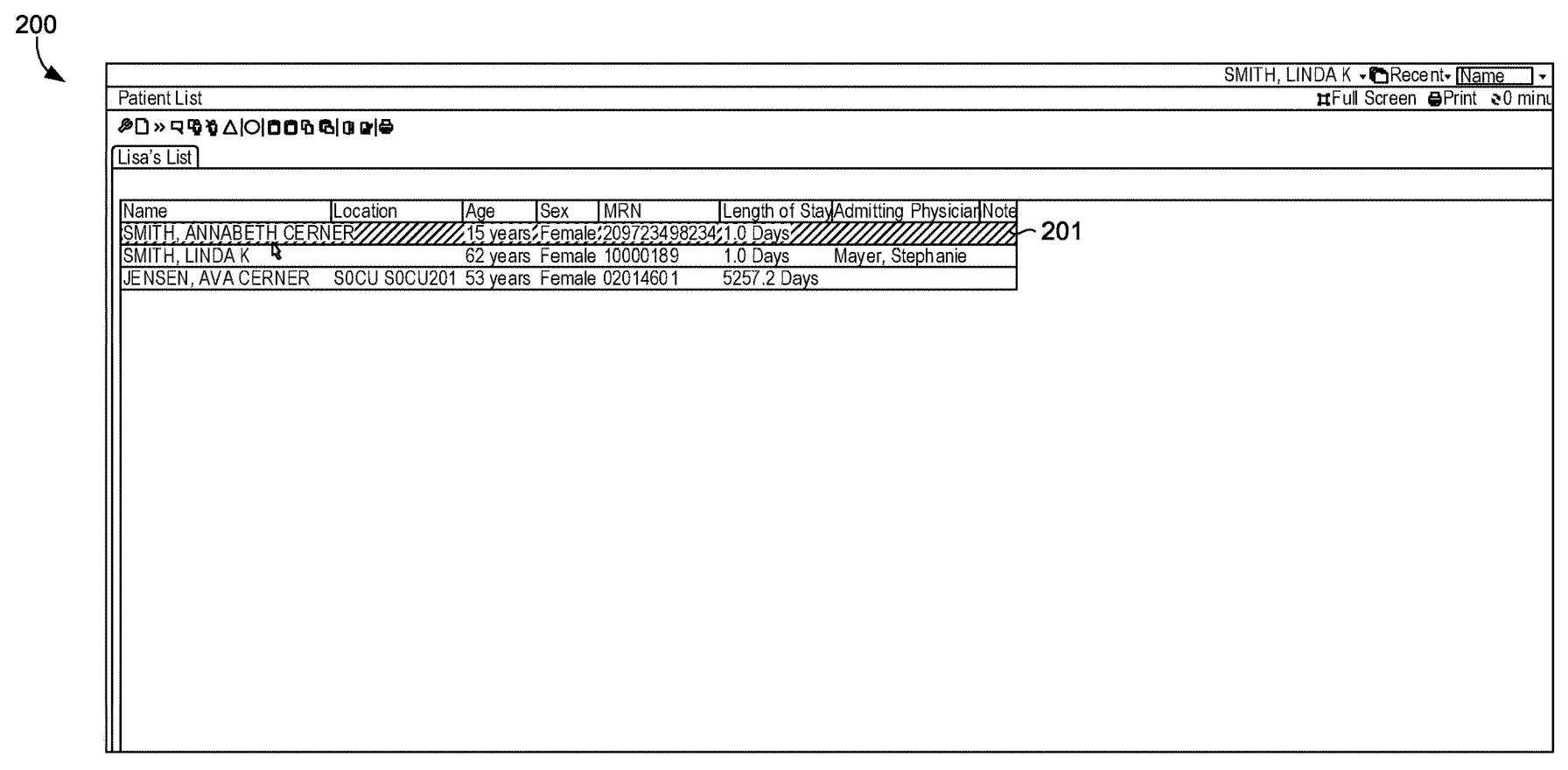
Figure 3:
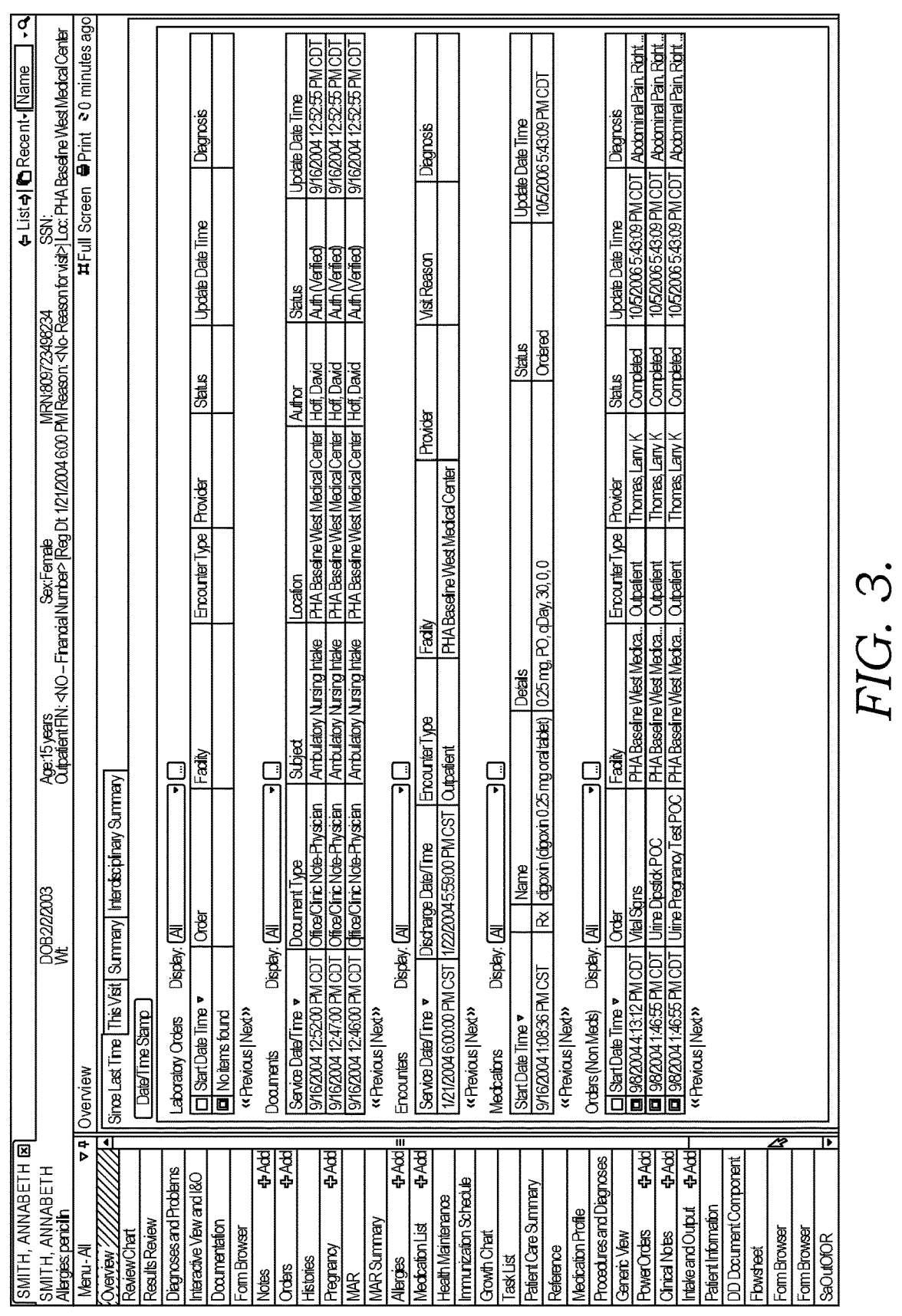
Figure 4:
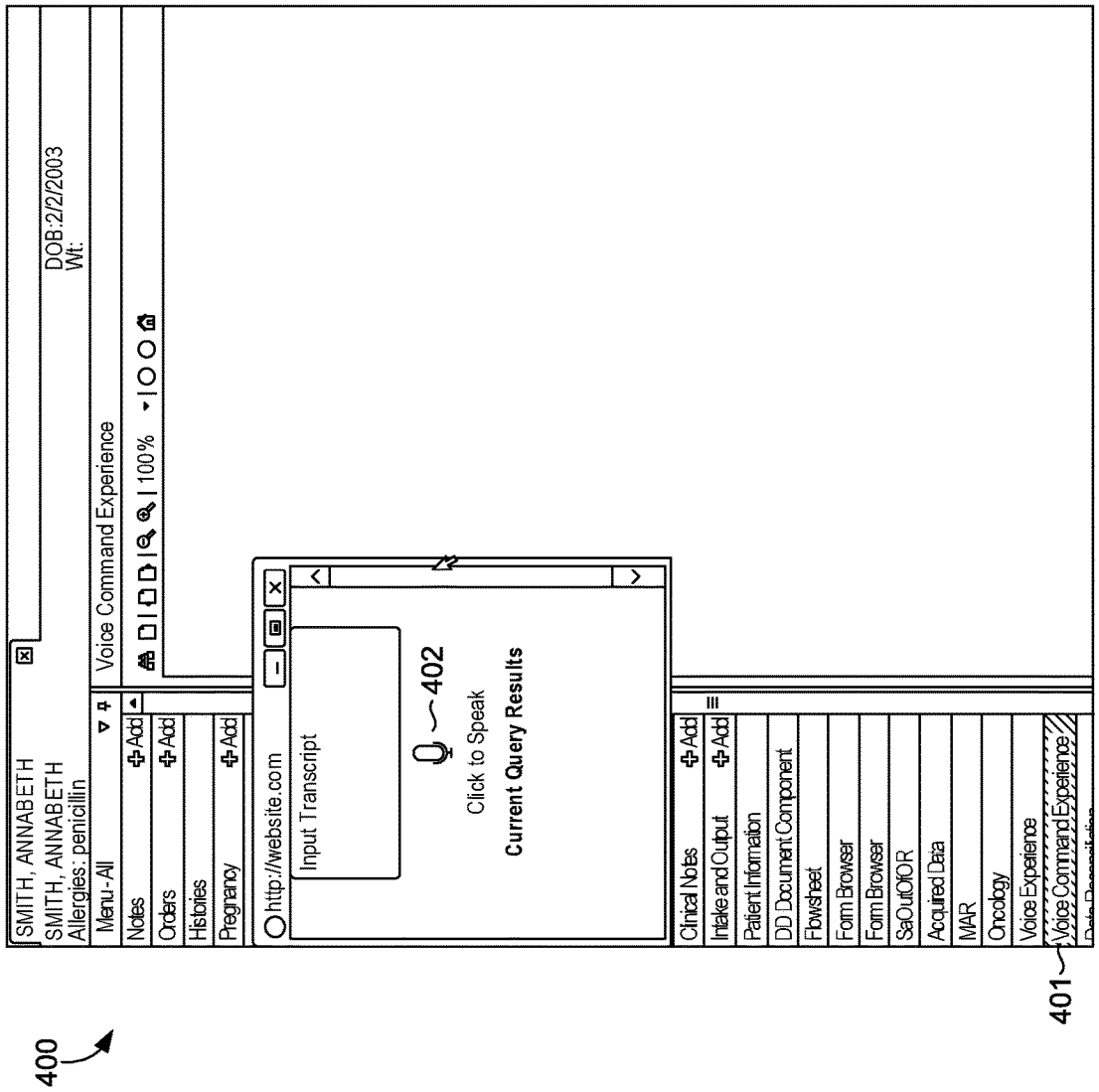

In some embodiments, the natural language processing is automatically performed while a user, such as a clinician, is having the voice conversation. In other embodiments, an indication to start natural language processing is received from an activate indication (e.g., "Hello, Scribe"), also referred to herein as an initiation cue. In either situation, a relevant patient/individual should be identified to associate with the captured voice inputs. An exemplary user interface 200 for selecting a relevant patient is provided in FIG. 2. As is shown, a patient 201 is selected from a list of patients. Upon selection, the electronic health record of the patient may be provided, as shown in interface 300 of FIG. 3. In the event the virtual scribe is not already listening to any voice inputs within an environment, an initiation cue can be provided, as illustrated in FIG. 4. A user can select a voice indicator 401 to provide an option to capture voice. An initiation cue can be provided by selection of an activate voice indicator 402.

Once activated and transcribed (speech to text functions), NLP is utilized to identify the clinical conditions within the voice input(s) and the system utilizes one or more clinical ontologies for the clinical conditions to identify one or more clinical concepts related to the clinical conditions. The clinical concepts are then classified into one or more classification groups. Classification groups, as used herein, refers generally to groupings of clinical concepts as defined in standardized formats. Standardized forms (including standard formats) are utilized today with standard locations including problems, diagnoses, medications, symptoms, procedures, etc. The standardized form locations may be used as a guide for the system to use to generate classification groups.

As used herein, a clinical ontology provides contextual relationships between a particular clinical condition and clinical concepts, such as evidence or symptoms of a clinical condition, treatment for the clinical condition (including procedures and medications), commonly co-existing conditions, risk factors for the clinical condition, and/or disqualifying evidence. The term "clinical ontology" as used herein is not intended to merely define a semantic hierarchy between concepts. Rather, a clinical ontology may provide one or more classifications comprising a set of clinical concepts that occur together within a patient's EHR as determined through one or more machine learning processes. The classifications may be the presence of clinical concepts that appear in association with a classification. For example, when a patient presents with a sore throat, the patient's record may reflect that the sore throat was the chief complaint or reason for the visit. The identified classifications are identified based on context in the voice conversation.

In some embodiments, multiple clinical conditions may be extracted from the voice conversation. A separate ontology may be used for each condition to identify additional concepts related to one particular concept. Accordingly, when multiple conditions are extracted from a voice conversation using NLP, multiple ontologies may be retrieved to identify concepts and classifications relevant to each condition.

Figure 5:
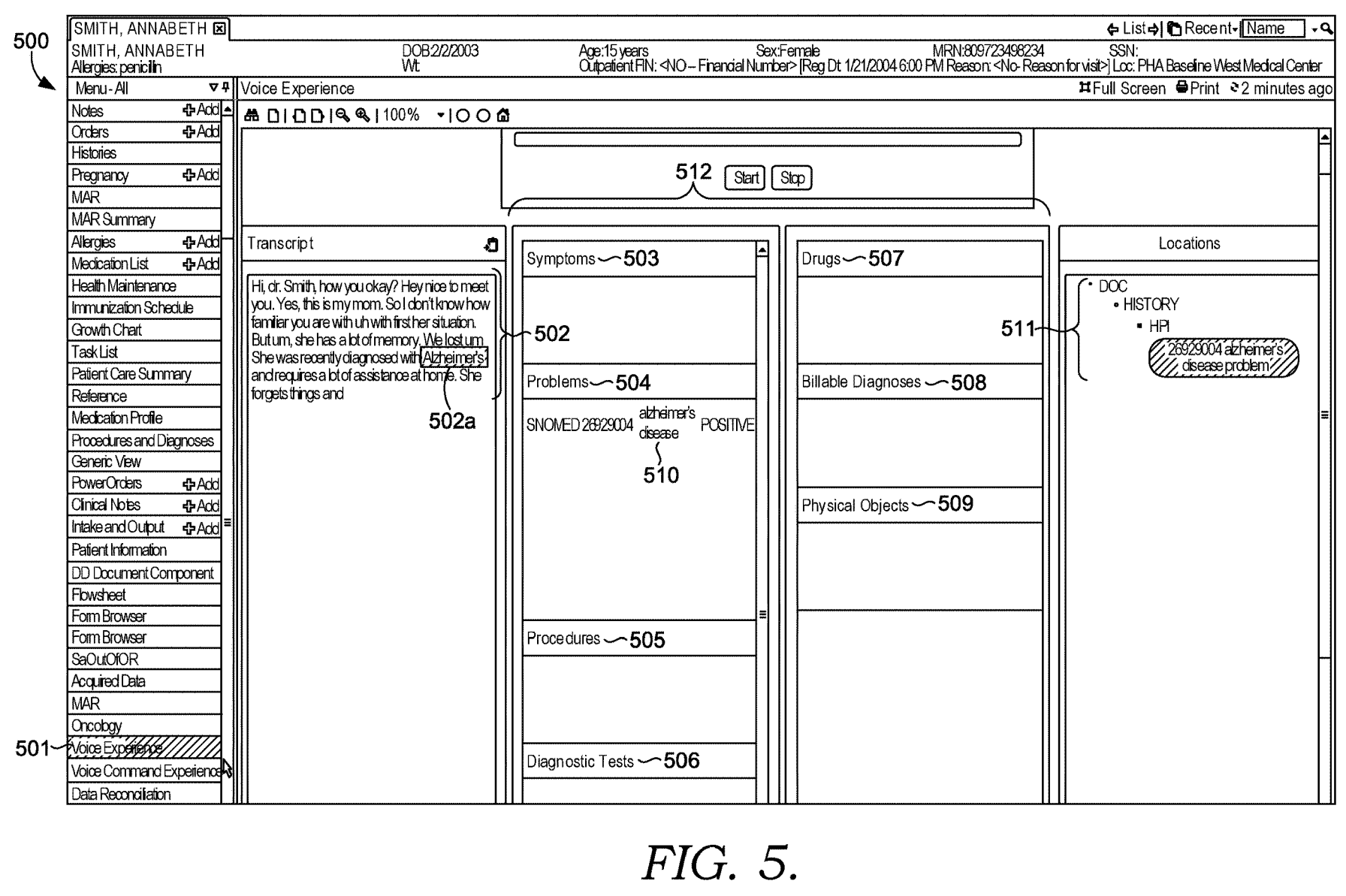
Figure 6:
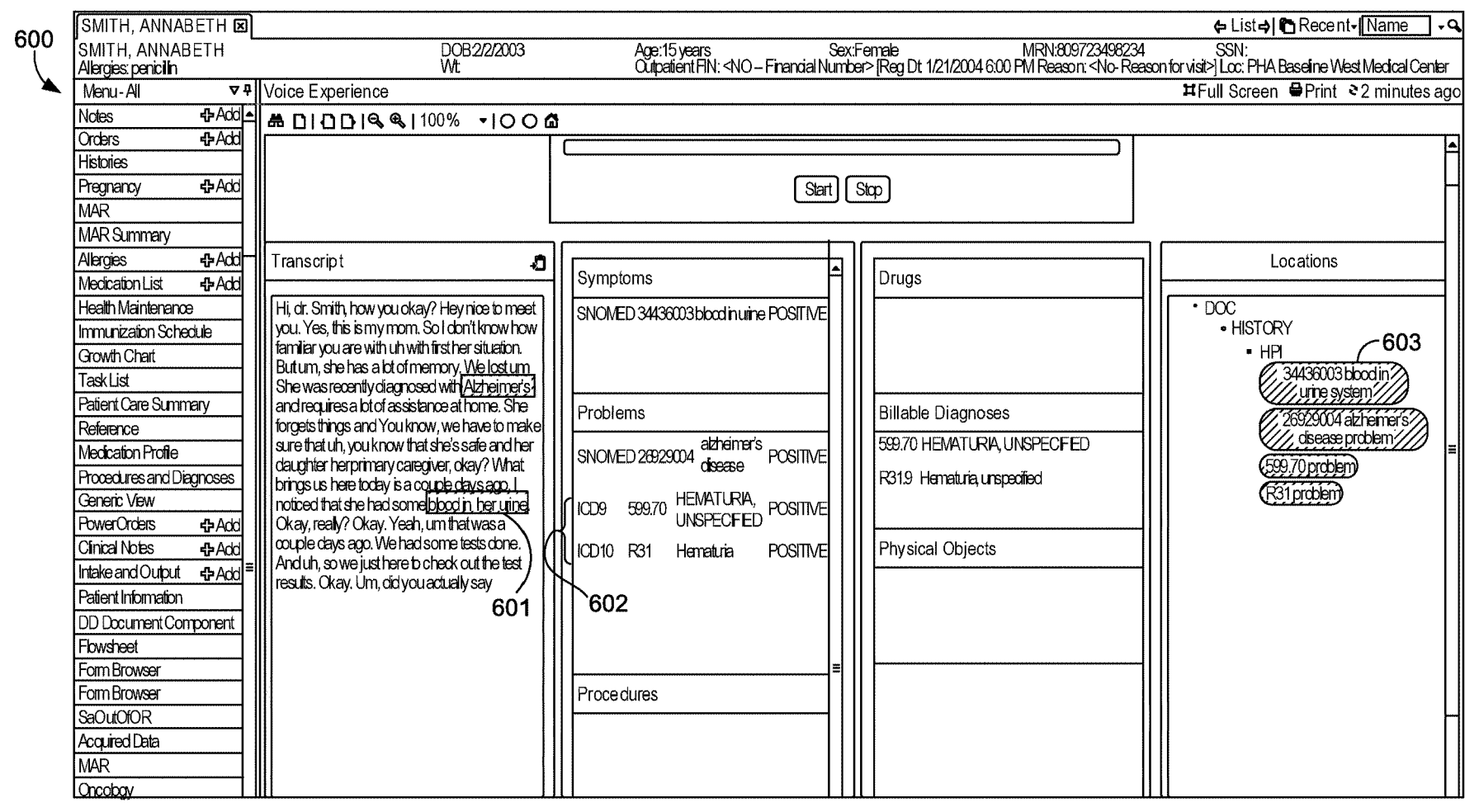

In an embodiment, once the clinical conditions are extracted and ontologies utilized to identify concepts, the one or more clinical concepts are "bucketized" into their respective classification groups and provided to a user. Additionally, the clinical concepts may be provided in an area of a user interface that illustrates a location within a structured document where the clinical concept may be documented (e.g., History of Present Illness (HPI), Exams, Review of Symptoms, Current Medications, Labs, Vital Signs, Past Medical History, Family History, Assessment and Plan, etc.). The items in the structured document area of the interface may be documented directly into the portion of the EHR that is designated within the structured document either automatically or manually (e.g., upon approval of a clinician). This is illustrated in FIG. 5, where an exemplary interface 500 is provided. The interface includes selection of a scribe at a scribe indicator 501. Once in the scribe interface, a transcript area 502 is provided that provides the transcript of the voice inputs. As previously mentioned, the transcript can be populated in real-time. Any clinical concepts identified within the transcript can be identified by, for instance, highlighting the concept, underlining or bolding the concept, adding an indicator next to the concept, or any other means that could visually mark the concept. Concept 502a has been highlighted to illustrate the meaning, but highlighting is not meant to be construed as the only way to depict a concept. As previously described, the classification groups can be provided and are shown in classification area 512 as classifiers 503-509. Classifier 504 (problems) has been populated with a concept 510 identified from the transcript. Finally, a location area 511 is provided that provides a location within a structured document where the clinical concept may be documented. A location can be provided for each clinical concept identified within the transcript. Here, Alzheimer's was identified as a problem and location area 511 provides the location where the identified concept can be documented within a patient's record. FIG. 6 provides an additional interface 600 illustrating that the scribe continues to add information to the transcript as additional voice inputs are received. As shown, an additional concept 601 has been identified in subsequent voice inputs and populated as items 602 in the problems area. Additionally, a location 603 is provided for the newly identified concept 601.

Figure 7:
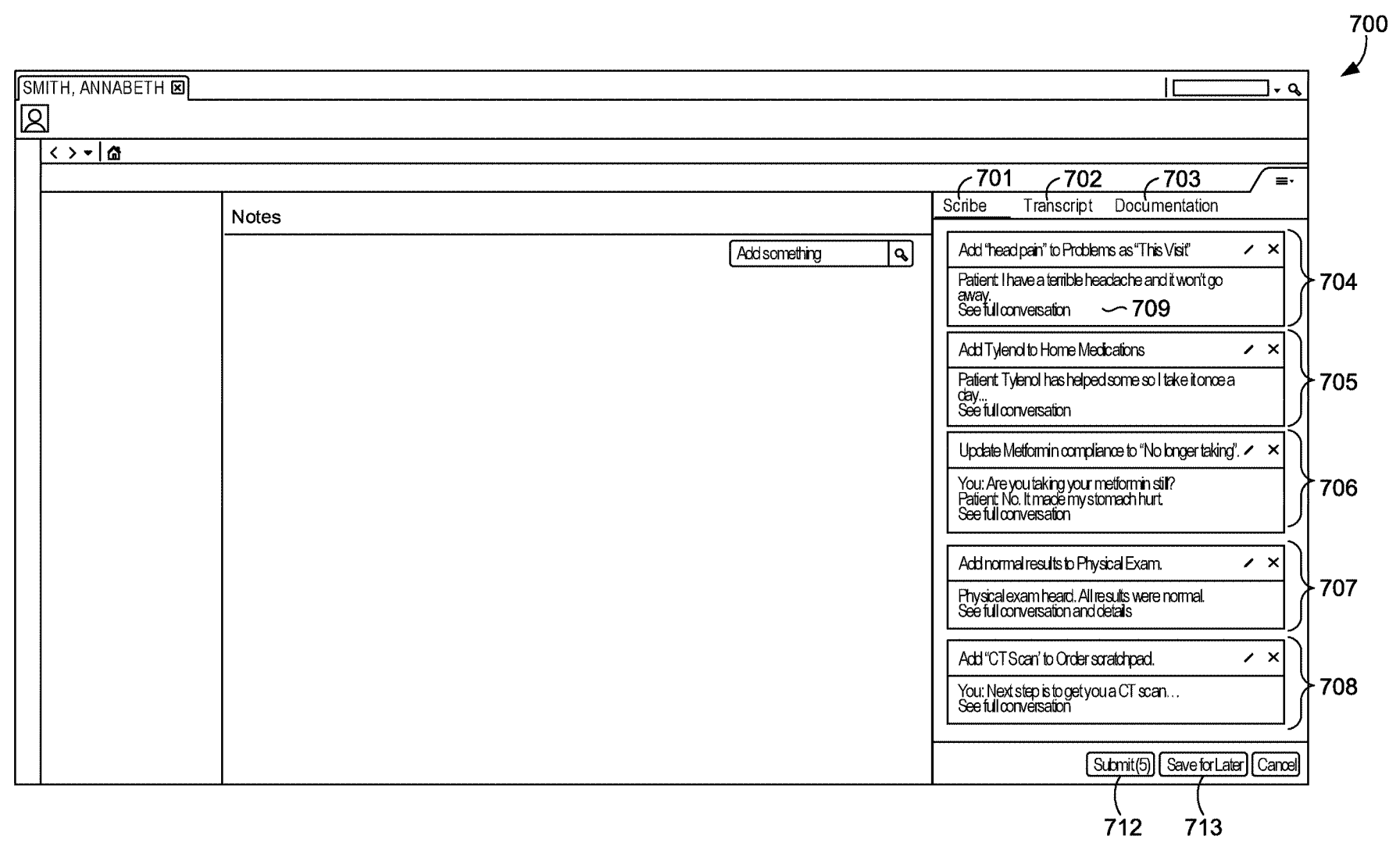
Figure 8:
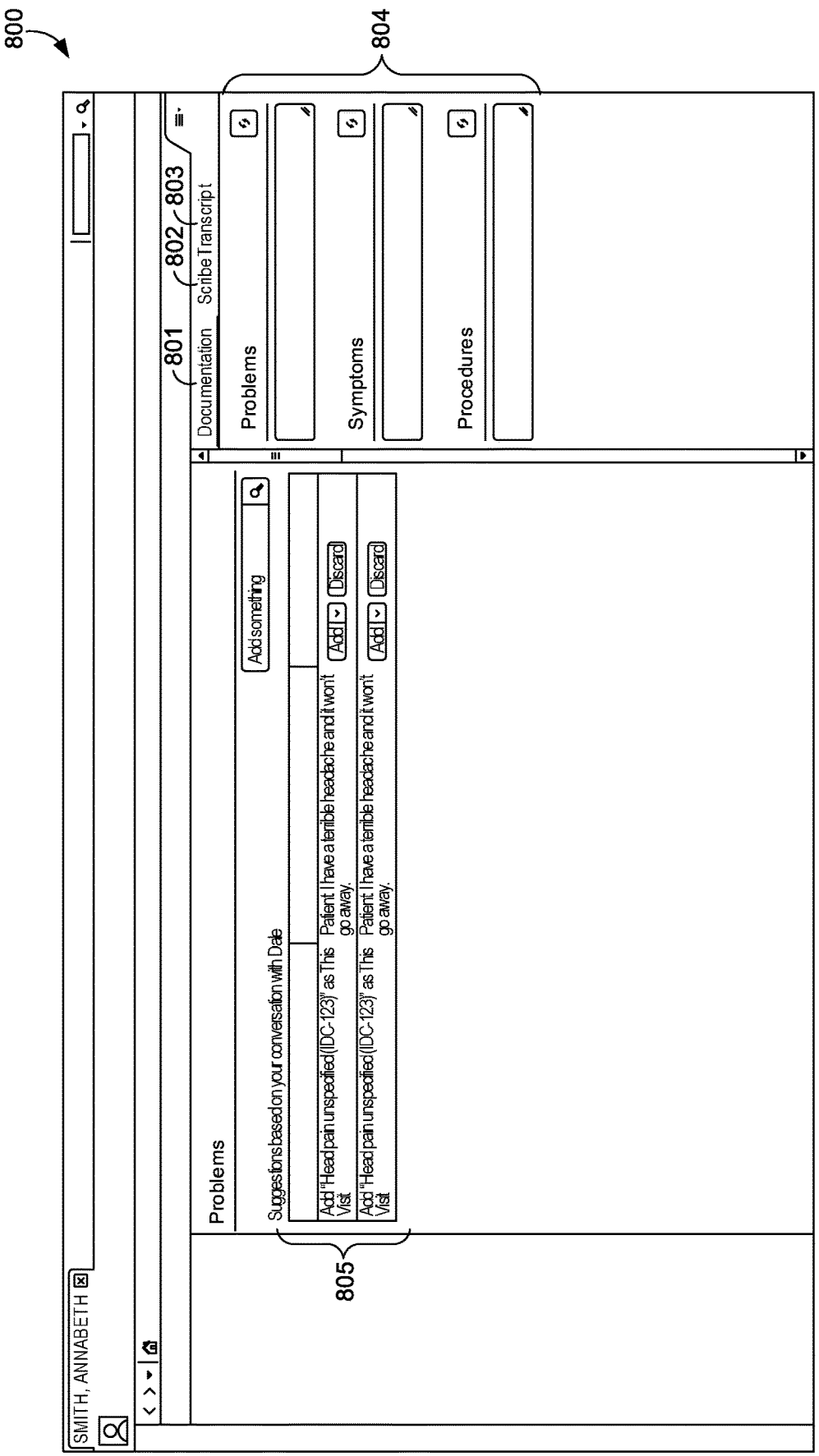

Alternative views are provided in FIGS. 7 and 8. In FIG. 7, an exemplary interface 700 is provided. This interface 700 provides for integration of the scribe interface in the workflow. A scribe indicator 701 can be selected to identify information identified from the scribe. The transcript indicator 702 can be selected to view a transcript of the voice inputs and a documentation indicator 703 can be selected to view one or more items to be documented. In FIG. 7, the scribe indicator 701 is currently selected. As is shown, items 704-708 are provided and were extracted from the voice inputs. Items 704-708 can include one or more clinical concepts and may further include a designation of one or more classification groups to which the clinical concepts belong. For example, item 704 is noted to potentially add to the "problems" list for the current visit. Each item includes a transcript expander such as expander 709. Selection of the expander results in navigation to the full transcript or at least a portion of the transcript related to the item with which the expander was found. A user has an option to submit selected items for consideration of documentation by selecting submit indicator 712. Selection of the submit indicator 712 will result in the system identifying one or more clinical concepts associated with the item (items 704-708). A user can also save items for later with selection of indicator 713.

FIG. 8 depicts an exemplary interface 800 illustrating selection of items for addition to one or more of a patient's record, a workflow, and the like. As with FIG. 7, documentation indicator 801, scribe indicator 802, and transcript indicator 803 are all available for selection to toggle between the three views. A documentation view is currently selected illustrating classification group area 804 where one or more items would be classified. Items 805 have been added to the problems note area for consideration for documentation. Items 805, as is shown, now include structured information along with the clinical concept identified. These can be selected to be added to the "problems" area in the documentation 801 screen for documentation in a patient's record.

Continuing on, validation sources, such as a patient's EHR, are used to verify that the conversation captured and output generated are complete and accurate. The one or more clinical concepts may be utilized with the patient's EHR to identify whether the scribe output is valid. By way of example, when asking a patient if they're taking any medications and they reply with "Yes, I'm taking Tylenol once daily", the medication section of the patient's EHR is analyzed to identify whether Tylenol is listed as a medication. If no, a notification that Tylenol is not currently listed may be provided. An indicator to add Tylenol to the patient's EHR may be provided in the notification. If yes, nothing may be provided or a notification that Tylenol is already listed and no changes are needed at this time may be provided.

In embodiments, when a discrepancy is identified between the scribe output and the patient's EHR data, actual values or data from the EHR may be provided so a clinician can easily review the discrepancy (rather than simply being notified that something is wrong). For example, an encounter having a patient reporting that they take a medication once daily that is noted in the chart as twice daily may be provided with a notification that the scribe data is not validated and the reason why is due to the frequency, while the portion of the record indication a twice daily dosage may be provided in the record for immediate viewing without navigating to any separate portions of the patient's record.

The EHR may be used to confirm or validate the scribe output of the voice conversation with data found in the current electronic documentation. The system may search for indicators of the one or more clinical concepts within the voice conversation and the EHR to determine whether the clinical concept within the voice conversation can be verified. In exemplary aspects, searching for indicators of the one or more clinical concepts comprises searching for structured data for the clinical concepts, such as measurements for physiological values or presence of a specific medication, laboratory, or procedure within the EHR.

In additional embodiments, various document formats may be generated from the voice conversation. One example document is structured and usable by the clinician with an aim to persist as part of the patient's record (e.g., doctor's notes). A second example document is transformed to a format consumable by the patient. The language and content may be tailored to the needs of the patient. A third example document may be tailored to the needs of referrals. For instance, if, during the voice conversation, a clinician recommends the patient meet with additional providers, a referral document may be generated.

In addition to documents, documentation items or action items may also be generated by the system. A documentation item or action item, as used herein, refers generally to data that would typically need to be documented in the patient's record either during or after the encounter. For example, patient's vital signs or other clinical findings need to be documented in the patient's record during a visit. Additionally, any orders or prescriptions a clinician provides need to be documented in the patient's record. The present system automatically generates these documentation items. For instance, if a clinician says "I'm putting you on a Z-pack"

the system intelligently knows that the clinician is placing an order ("putting you on" may be a cue that an order is to follow) for a medication. The prescription may be automatically generated by the scribe/system and populated on the user interface. From there, it may be automatically documented in the patient's record or it may be pending until signed or manually approved by the clinician. In additional embodiments, the system is linked to other programs such that it may be communicated automatically or post-approval to an appropriate destination. For example, a medication prescription may be sent to the pharmacy or an order for a chest x-ray may be sent to radiology.

In embodiments, the system identifies relevant information from an external source and provides that information upon identifying, within the voice conversation, a reference to the information. For instance, if a clinician states "I reviewed your vitals, they look good," then the system may identify the clinical concept "vitals" and provide the collected vital signs on a user interface, within a document, and the like. This information may be extracted from the patient's EHR. The information may also be identified from other devices, such as a heart monitor, etc., that may be associated with a patient.

Direct voice commands may also be utilized with the present system. For instance, a clinician may state "show me their vaccinations" to view a patient's vaccinations. Again, the system may extract this information from a patient's EHR or any other records associated with the patient. The system may be integrated with the patient's EHR such that the portion of the record is directly shown or a link thereto may be provided.

In additional embodiments, data other than voice may be captured during the encounter, such as movement, images, sensor data, videos, etc. This data may be captured and incorporated directly into the EHR and, thus, can be referenced during subsequent visits. For example, movement data (e.g., via sensors or a video) may be captured and used at a follow-up visit in three months to compare a gait. Various in-room sensors may be used to capture data and include, but are not limited to, cameras, speakers, microphones, 3D cameras, wearable sensors, connected devices, and the like.

Figure 9:
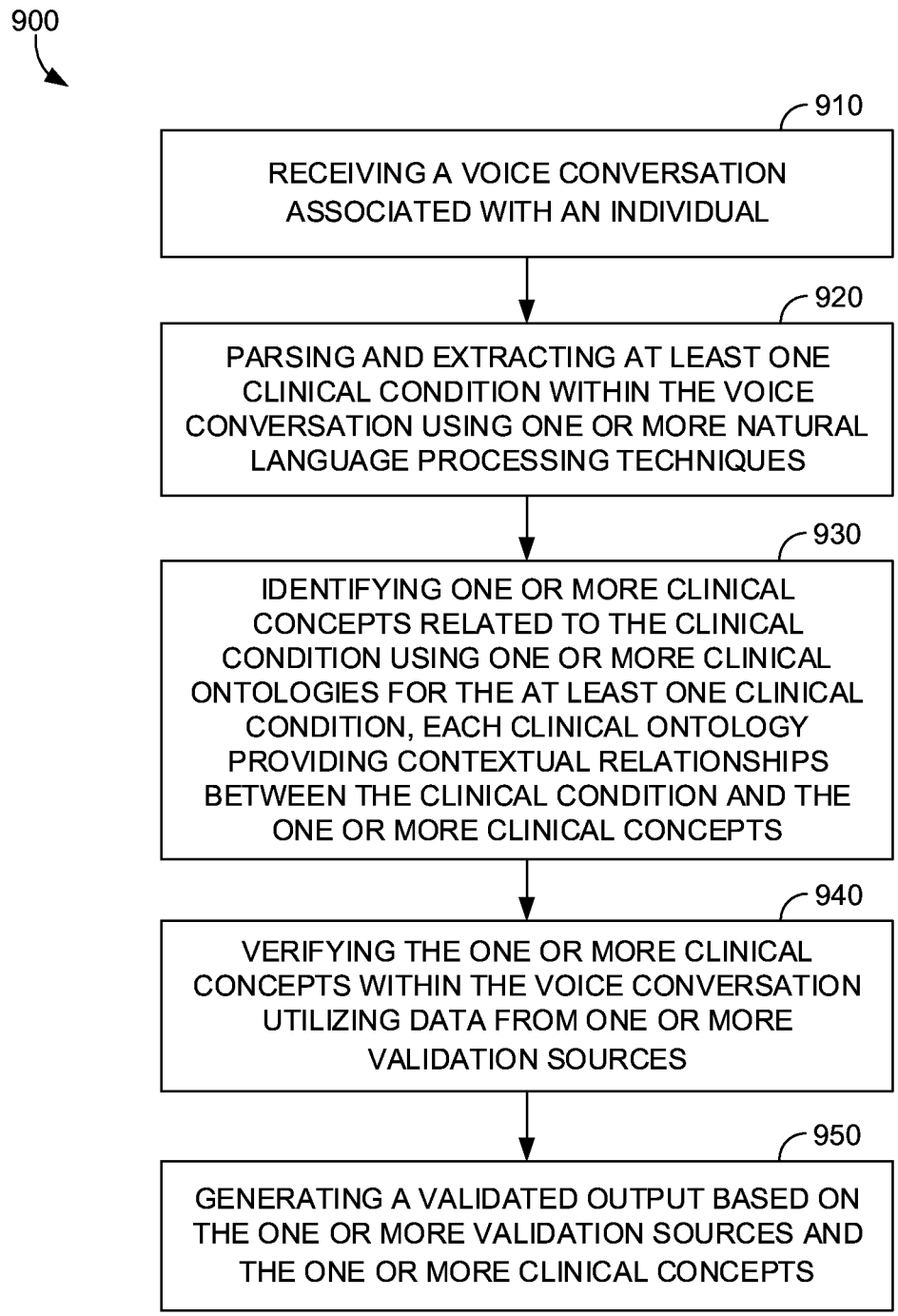
FIGS. 9 and 10 depict exemplary flows of methods for performing natural language understanding on voice conversations, in accordance with embodiments herein.

Turning now to FIG. 9, an exemplary flow diagram of a method 900 for performing natural language understanding on voice conversations is provided. Initially, at block 910, a voice conversation associated with an individual is received. The voice conversation can include a plurality of voice inputs. At block 920, at least one clinical condition within the voice conversation is parsed and extracted using one or more natural language processing techniques. One or more clinical concepts related to the clinical condition is identified at block 930 using one or more clinical ontologies for the at least one clinical condition. Each clinical ontology can provide contextual relationships between the clinical condition and the one or more clinical concepts. At block 940, the one or more clinical concepts within the voice conversation is verified utilizing data from one or more validation sources. A validated output is generated based on the one or more validation sources and the one or more clinical concepts at block 950.

Figure 10:
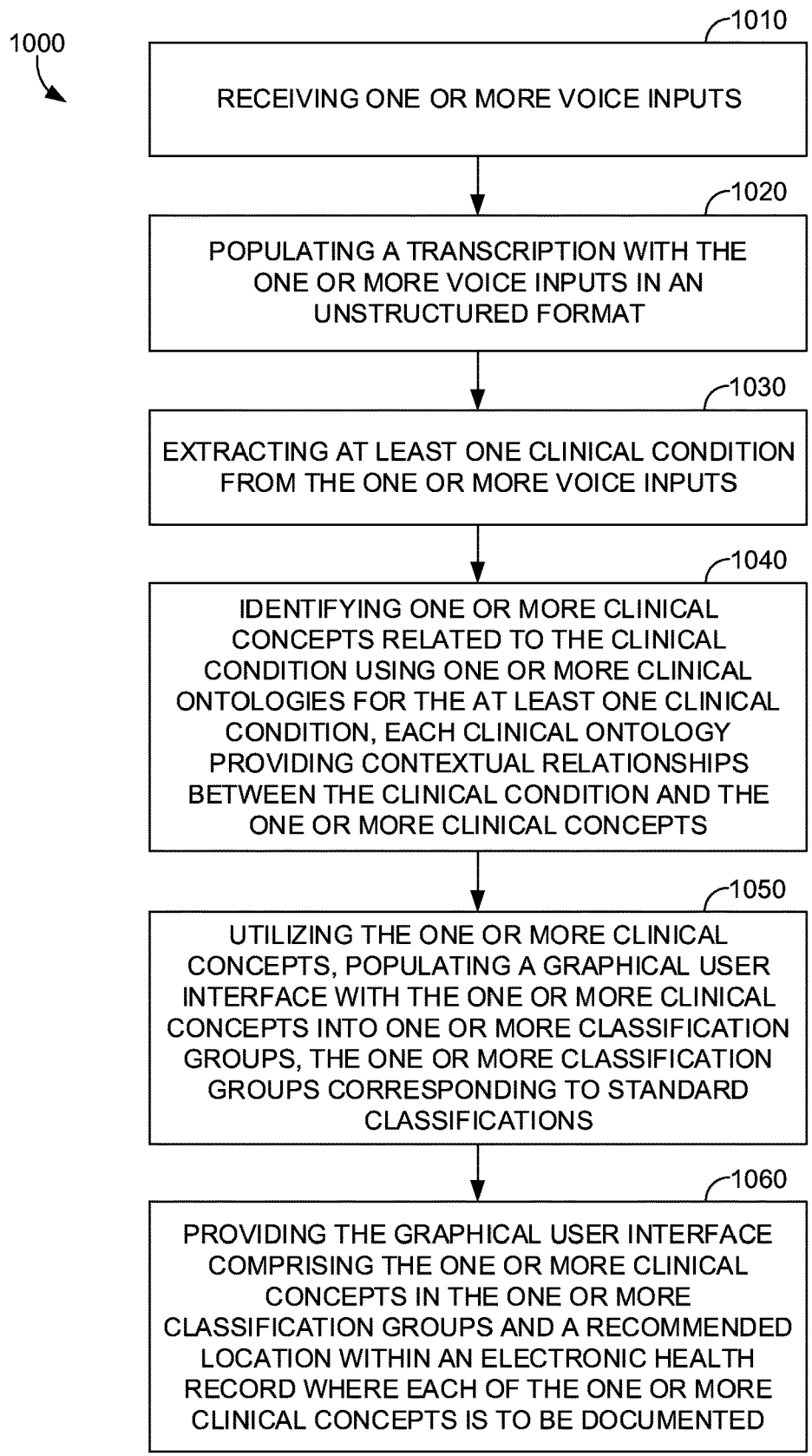

Turning now to FIG. 10, an exemplary flow diagram of a method 1000 for performing natural language understanding on voice conversations is provided. Initially, at block 1010, one or more voice inputs is received. A transcript with the one or more voice inputs in an unstructured format is populated at block 1020. At block 1030, at least one clinical condition is extracted from the one or more voice inputs. At block 1040, one or more clinical concepts related to the clinical condition is identified using one or more clinical ontologies for the at least one clinical condition, each clinical ontology providing contextual relationships between the clinical condition and the one or more clinical concepts. At block 1050, utilizing the one or more clinical concepts, a graphical user interface is populated with the one or more clinical concepts into one or more classification groups, the one or more classification groups corresponding to standard classifications. At block 1060, the graphical user interface is provided comprising the one or more clinical concepts in the one or more classification groups and a recommended location within an electronic health record where each of the one or more clinical concepts is to be documented.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more non-transitory computer-readable media having computer-executable instructions embodied thereon that when executed, provide a method for enhanced natural language processing, the method comprising:
   receiving one or more voice inputs;
   segmenting the one or more voice inputs into a plurality of segments using a preconfigured threshold;
   populating a transcription with the one or more voice inputs in an unstructured format, wherein the transcription is populated by stitching the plurality of segments into a sequence;
   extracting at least one clinical condition from the one or more voice inputs;
   validating the at least one clinical condition extracted when the at least one clinical condition is determined to correlate to structured data in a patient's electronic health record;
   identifying one or more clinical concepts related to the clinical condition using one or more clinical ontologies for the at least one clinical condition, each clinical ontology providing contextual relationships between the clinical condition and the one or more clinical concepts;
   utilizing the one or more clinical concepts, populating a graphical user interface with the one or more clinical concepts into one or more classification groups, the one or more classification groups corresponding to standard classifications;
   providing the graphical user interface comprising the one or more clinical concepts in the one or more classification groups and a recommended location within the patient's electronic health record where each of the one or more clinical concepts is to be documented; and
   providing a notification of an error, wherein the notification includes each of the error, at least a portion of the one or more voice inputs related to the error, and at least a portion of data from one or more validation sources conflicting with the one or more voice inputs.

2. The media of claim 1, wherein the method further comprises validating the one or more voice inputs with the one or more validation sources.

3. The media of claim 2, wherein the one or more validation sources comprises an electronic health record for an individual associated with the one or more voice inputs.

4. The media of claim 2, wherein the one or more validation sources is an integrated device associated with an individual associated with the one or more voice inputs.

5. The media of claim 1, wherein the one or more classification groups includes at least problems.

6. The media of claim 1, wherein the standard classifications are defined by a standard utilized by a source system associated with a facility in which the one or more voice inputs are identified.

7. A computerized method, the method comprising:
receiving one or more voice inputs;
segmenting the one or more voice inputs into a plurality of segments using a preconfigured threshold;
populating a transcription with the one or more voice inputs in an unstructured format, wherein the transcription is populated by stitching the plurality of segments into a sequence;
extracting at least one clinical condition from the one or more voice inputs;
validating the at least one clinical condition extracted when the at least one clinical condition is determined to correlate to structured data in a patient's electronic health record;
identifying one or more clinical concepts related to the clinical condition using one or more clinical ontologies for the at least one clinical condition, each clinical ontology providing contextual relationships between the clinical condition and the one or more clinical concepts;
utilizing the one or more clinical concepts, populating a graphical user interface with the one or more clinical concepts into one or more classification groups, the one or more classification groups corresponding to standard classifications;
providing the graphical user interface comprising the one or more clinical concepts in the one or more classification groups and a recommended location within the patient's electronic health record where each of the one or more clinical concepts is to be documented; and
providing a notification of an error, wherein the notification includes each of the error, at least a portion of the one or more voice inputs related to the error, and at least a portion of data from one or more validation sources conflicting with the one or more voice inputs.

8. The method of claim 7, wherein the method further comprises validating the one or more voice inputs with the one or more validation sources.

9. The method of claim 8, wherein the one or more validation sources comprises an electronic health record for an individual associated with the one or more voice inputs.

10. The method of claim 8, wherein the one or more validation sources is an integrated device associated with an individual associated with the one or more voice inputs.

11. The method of claim 8, further comprising identifying an error within the one or more voice inputs based on the one or more validation sources.

12. The method of claim 7, wherein the one or more classification groups includes at least problems.

13. The method of claim 12, wherein the standard classifications are defined by a standard utilized by a source system associated with a facility in which the one or more voice inputs are identified.

14. A system comprising:
one or more processors to:
receive one or more voice inputs;
segmenting the one or more voice inputs into a plurality of segments using a preconfigured threshold;
populate a transcription with the one or more voice inputs in a n unstructured format, wherein the transcription is populated by stitching the plurality of segments into a sequence;
extract at least one clinical condition from the one or more voice inputs;
validate the at least one clinical condition extracted when the at least one clinical condition is determined to correlate to structured data in a patient's electronic health record;
identify one or more clinical concepts related to the clinical condition using one or more clinical ontologies for the at least one clinical condition, each clinical ontology providing contextual relationships between the clinical condition and the one or more clinical concepts;
utilize the one or more clinical concepts, populating a graphical user interface with the one or more clinical concepts into one or more classification groups, the one or more classification groups corresponding to standard classifications;
provide the graphical user interface comprising the one or more clinical concepts in the one or more classification groups and a recommended location within the patient's electronic health record where each of the one or more clinical concepts is to be documented; and
providing a notification of an error, wherein the notification includes each of the error, at least a portion of the one or more voice inputs related to the error, and at least a portion of data from one or more validation sources conflicting with the one or more voice inputs.

\* \* \* \* \*

UNITED STATES PATENT AND TRADEMARK OFFICE
CERTIFICATE OF CORRECTION

PATENT NO. : 11,398,232 B1
APPLICATION NO. : 16/720641
DATED : July 26, 2022
INVENTOR(S) : Emin Agassi and Tanuj Gupta It is certified that error appears in the above-identified patent and that said Letters Patent is hereby corrected as shown below:

In the Claims

Claim 14, Column 18, Line 24:
The line reading "in a n unstructured format, wherein the transcription is" should read --in an unstructured format, wherein the transcription is--.

Signed and Sealed this
Sixth Day of September, 2022

*Katherine Kelly Vidal*
Katherine Kelly Vidal
*Director of the United States Patent and Trademark Office*